(12) United States Patent
Karatani

(10) Patent No.: US 11,879,148 B2
(45) Date of Patent: Jan. 23, 2024

(54) METHODS FOR DETECTION, DETERMINATION, AND ACTIVITY MEASUREMENT OF PEROXIDASE BASED ON CHEMILUMINESCENCE

(71) Applicant: KYOTO LUMINOUS SCIENCE LABORATORY, Kyoto (JP)

(72) Inventor: Hajime Karatani, Kyoto (JP)

(73) Assignee: KYOTO LUMINOUS SCIENCE LABORATORY, Kyoto (JP)

( * ) Notice: Subject to any disclaimer, the term of this patent is extended or adjusted under 35 U.S.C. 154(b) by 0 days.

(21) Appl. No.: 17/733,531

(22) Filed: Apr. 29, 2022

(65) Prior Publication Data

US 2022/0348980 A1 Nov. 3, 2022

(30) Foreign Application Priority Data

Apr. 30, 2021 (JP) .................................. 2021-99761

(51) Int. Cl.
*C12Q 1/28* (2006.01)
(52) U.S. Cl.
CPC ...................................... *C12Q 1/28* (2013.01)
(58) Field of Classification Search
CPC ....................................................... C12Q 1/28
See application file for complete search history.

(56) References Cited

U.S. PATENT DOCUMENTS 6,432,662 B1 8/2002 Davis et al.

FOREIGN PATENT DOCUMENTS

JP 2011-043447 A 3/2011

OTHER PUBLICATIONS

Collaudin et al., "Investigations of the Enhancer Effect of a High-Salt Concentration Medium on the Luminol Chemiluminescent Reaction", Photochemistry and Photobiology, 1997, vol. 65, No. 2, pp. 303-308. (Year: 1997).*
Banu et al., "Luminol chemiluminescence induced by immobilized xanthine oxidase", Analytica Chimica Acta, 2005, vol. 541, pp. 91-97. (Year: 2005).*
Karatani., "Luminol-hydrogen peroxide-horseradish peroxidase chemiluminescence intensification by kosmotrope ammonium sulfate", Analytical Sciences, 2022, vol. 38, pp. 613-621. (Year: 2022).*

* cited by examiner

*Primary Examiner* — Satyendra K Singh
(74) *Attorney, Agent, or Firm* — Sughrue Mion, PLLC

(57) ABSTRACT

A further high-sensitive method for detection, determination, and activity measurement of peroxidase with no special enhancer argent. The substance, for example, high-concentration ammonium sulfate, is dissolved in the reaction solution to give rise to the micro-hydrophobic property, for detection, determination, and activity measurement of peroxidase using luminol and hydrogen peroxide as substrates.

3 Claims, 11 Drawing Sheets

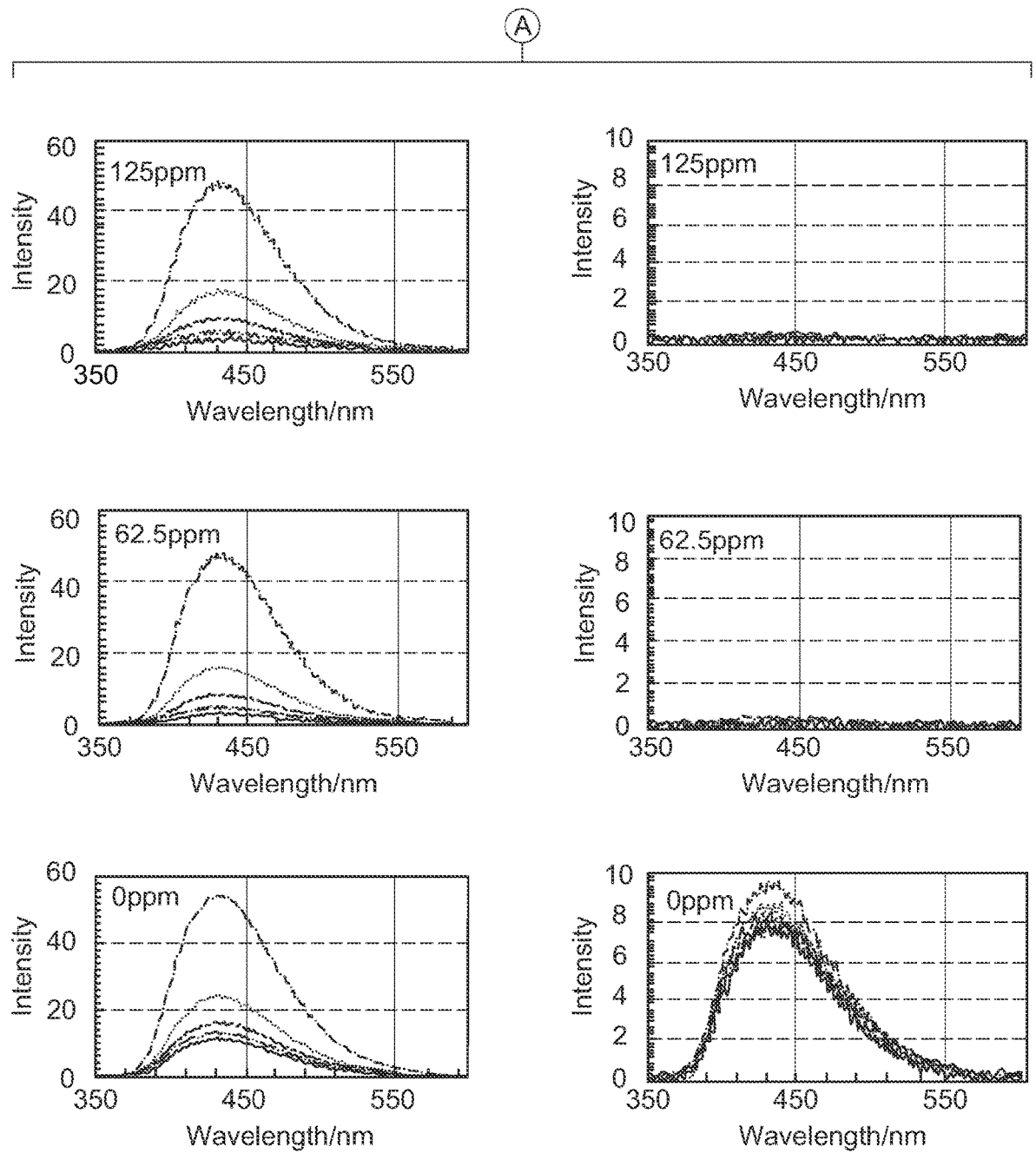
FIG. 4 (Continued...)

Dissociation of luminol

Luminol monoanion (LH⁻)

First step of the reaction of HRP with $H_2O_2$

Reaction of LH⁻ with Compound I

Reaction of another LH⁻ with Compound II (Regeneration of HRP)

(A)

Disproportionation of L⁻ to prepare luminol diazaquinone
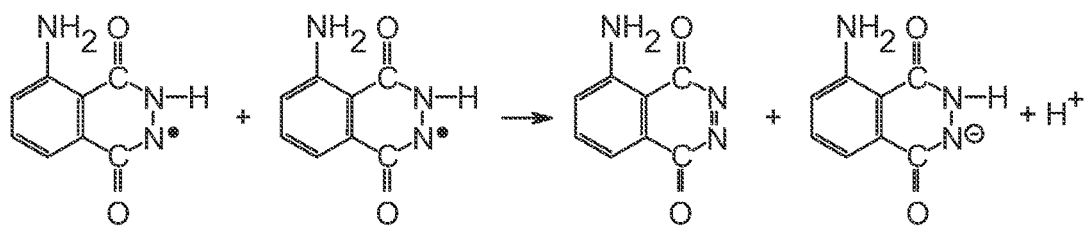
Addition of HOOH, followed by the formation of luminol dixetane product
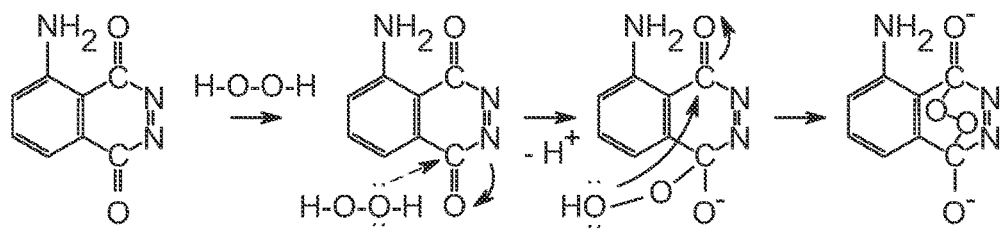
Cleavage of dioxetane, followed by the formation of light emission
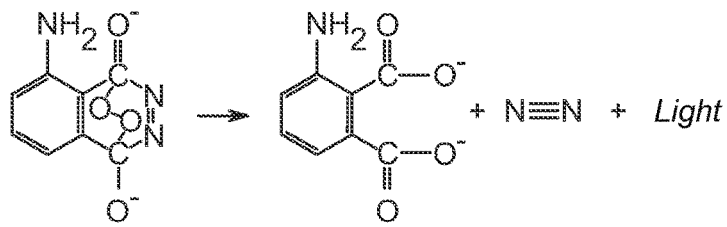
FIG. 5 (Continued...)

METHODS FOR DETECTION, DETERMINATION, AND ACTIVITY MEASUREMENT OF PEROXIDASE BASED ON CHEMILUMINESCENCE

TECHNICAL FIELD

The present invention relates to the methods for detection, determination, and activity assay of peroxidase using luminol as its substrate.

BACKGROUND ART

To assay the antigen-antibody interaction, i.e., immunoassay, it is necessary to discriminate the antigen-antibody complex neither from the unreacted antigen nor from the unreacted antibody. To this end, the target antibody or antigen is labeled with a suitable labeling agent, followed by the selective measurement of the labelled antigen-antibody complex. As labeling agents, materials, have been utilized for the selective measurement in the antigen-antibody interaction, are as follows; radioisotopes, enzymes, fluorescent substances, chemiluminescent substances, coloring substances, metal complexes, electrochemically active substances, and so on. As a manner to use enzyme as a labeling agent, peroxidase and alkaline phosphatase are major players, both of which react with coloring substrates to gives specific color corresponding to the concentration of enzymes labeled either with antigen or with antibody. Furthermore, these enzymes enable to catalyze chemiluminescent and fluorescent reactions with the chemiluminescent and fluorescent substrates. Based on these reactions, Chemiluminescence Enzyme Immunoassay (CLEIA) and Fluorescent Enzyme Immunoassay (FEIA) have been developed. On the other hand, Chemiluminescent Immunoassay (CLIA) has also been used. This method utilizes chemiluminescent labeling agent which produce light emission in the absence of enzymes that are usually susceptible to the thermal denaturation. For example, luminol and ruthenium(II) complex are utilized. Regarding non-enzymatic light induction, the electrochemically chemiluminescence induced on the electrode has also been applied for the immunoassay using with antigen or antibody labeled directly with either luminol derivative or ruthenium(II) complex derivative as a labeling agent and has been called Electrochemiluminescent Immunoassay (ECLIA).

These methods described above have been applied practically for high sensitive immunoassay to date.

Among the methods described in the said column [0002], the peroxidase catalyzed luminol chemiluminescence is most frequently utilized in immunoassay. Briefly, luminol reacts with hydrogen peroxide in the presence of peroxidase to produce light emission via the production of luminol intermediate. It was found that this chemiluminescence was strongly enhanced in the presence of p-substituted phenol, such as 4-iodophenol (Non-Patent Document, 1-4). This enhanced chemiluminescence is called Enhanced Chemiluminescence (ECL). From then onward, many efforts have been devoted to developing the peroxidase catalyzed luminol chemiluminescence with p-substituted phenol with the aim of further enhancing the light emission.

The features of ECL are as follows: the reaction between the two-electron oxidized peroxidase intermediate and p-substituted phenol efficiently produces p-substituted phenoxy radical. The produced phenoxy radicals efficiently react with luminol, existing in monoanion form, to be converted to luminol diazoquinone intermediate, followed by the reaction with hydrogen peroxide existing in large excess. Finally, 3-aminophthalic dianion in the excited state is formed via formation of another intermediate, resulting in the light emission, when the excited emitter goes back to the ground state. Thus, the luminol chemiluminescence is enhanced by virtue of the participation of adequate p-substituted phenoxy. That is to say, the reason that p-substituted phenols are useful as chemiluminescence enhancer is explained by the idea that the formation of a key luminol azaquinone intermediate is increasingly facilitated by the phenoxy radical, efficiently produced by the peroxidase reaction with p-substituted phenoxy.

Moreover, high-performance enhancer has been developed, superseding p-substituted phenol (Patent Document 1, 2).

PRIOR ART DOCUMENTS

Non-Patent Documents

[Non-Patent Document 1] B. B. Kim, et al., Analytical Biochemistry, 199, 1-6 (1991)
[Non-Patent Document 2] M. Kjalke, et al., Biochim. Biophys. Acta, 1992, April 17; 1120(3): 248-256.
[Non-Patent Document 3] G. H. Thorpe and L. J. Kricka, Methods in Enzymology 133, 331-353 (1986)
[Non-Patent Document 4] G. H. G. Thorpe, L. J. Kricka, et al., Anal. Biochem., 145, 96 (1985)

Patent Documents

[Patent Document 1] Japanese Patent Publication No. 2011-43447
[Patent Document 2] Japanese Patent Publication No. H2-291299

SUMMARY OF INVENTION

Problems to be Resolved by the Invention

Although the luminol chemiluminescence with enhancer described above has made long lasting and strong emission feasible, it is necessary to prepare special enhancer agent. It is also necessary to use organic solvent to resolve the nearly insoluble enhancer molecule for the preparation of the luminol solution. Furthermore, the realization of stronger and more persistent chemiluminescence is required for the detection of trace amounts of POD labeled to either antigen or antibody.

Means for Solving the Problems

As a result of the research to achieve higher sensitive system for the detection and determination of peroxidase, the inventor has found out that the chemiluminescence arising from the luminol-hydrogen peroxide-peroxidase reaction is considerably intensified by dissolving the substance, which gives rise to the hydrophobic microenvironment in the aqueous luminol reaction system, and has completed the present invention.

That is, in the present invention, it has been found out that the aforementioned substance, which is water-soluble itself and gives rise to the hydrophobic property in aqueous system, facilitates not only the coordination of hydrogen peroxide onto the active site of peroxidase but also the nucleophilic reaction between luminol diazoquinone intermediate and hydrogen peroxide. This discovery has led the present invention.

As substances giving rise to the hydrophobic property in aqueous solution, by dissolving them in aqueous solution it is essential to generate ammonium ion, magnesium ion, sodium ion, and so on, as cations, and on the other hand, to generate sulfate ion, acetate ion, iodide ion, chloride ion, and so on, as anions, all of which show strong salting out effect, i.e., anti-chaotropic (kosmotropic) ions. As a cation, the effect of ammonium ion is superior to the others, and ammonium sulfate, ammonium acetate, and so on are considered. On the other hand, focusing on anions, following salts are considered: as salts containing sulfate ion, ammonium sulfate, sodium sulfate, magnesium sulfate, and so on; as salts containing acetate ion, ammonium acetate, sodium acetate, and so on; and salts containing chloride ion, ammonium chloride, sodium chloride, and so on. Among the salts above-mentioned, it is particularly desirable to use ammonium sulfate.

Moreover, other than inorganic salts described above, it is possible to use substances, such as glycerol and polyethylene glycol, to form hydrophobic microenvironment in aqueous solution.

In the case of using ammonium sulfate, high concentration ammonium sulfate is desirable and its concentration range is between 3.0 M and 4.0 M, especially the concentration of 3-3.5 M is more desirable. In the light of the solubility, approximately 3.5 M ammonium sulfate is suitable for practical use.

Moreover, in the present invention, its is desirable to use ethylenediamine tetraacetate (EDTA) together with ammonium sulfate. By dissolving EDTA in the reaction solution, background chemiluminescence can be removed almost completely. The amount of addition of EDTA is greater than 60.0 ppm and lower than 5000 ppm, albeit the amount depends on the ammonium sulfate concentration. Preferably, the addition amount ranges between 62.5 ppm and 500 ppm.

The chemiluminescence measurement based on the present invention can be applied without restriction on the measurement object and the measurement method in the case that peroxidase is used as an enzyme and at the same time chemiluminescent substrate, oxidizing agent and salts providing anti-chaotropic ions are used for the detection, determination and the activity measurement of peroxidase. For example, as a specific binding reaction system using peroxidase as a labeling enzyme, it can be applied to various enzyme linked immunoassays, using the primary antibody method, the secondary antibody method, the competitive assay, the sandwich assay, the homogeneous assay, the heterogeneous assay, the western blot assay, DNA probe assay, and so on.

Peroxidase (POD) available in the present invention is not restricted to a special source. Peroxidases isolated from horse radish, microorganisms, cow milk, white blood cells and so on are available. Among them, peroxidase isolated from horse radish (HRP) is preferable. Peroxidase can be utilized not only in a free state but also in a state of the complex bound to a suitable ligand, such as antigen, antibody, hapten, protein A, avidin, biotin, and so on.

Based on the present invention, the proper usage of POD required in the present method is the amount that gives rise to the linear relationship between the amount of POD and the resultant chemiluminescence intensity. In particular, the adequate usage of POD in the reaction mixture is ranging in concentration between pM and nM. When POD concentration is lower than this range, the effect of the present invention lowers, and on the other hand, when the POD concentration is higher than this range, the conventional POD catalyzed luminol chemiluminescence is available and no necessary to apply the present high-sensitive luminol chemiluminescence provided by the present invention.

POD is available not only in a free state but also in a state labeled to insoluble carriers. As carriers, conventionally known carriers are available, that is, beads, tubes, and microparticles, made of polymer material such as polystyrene. Additionally, as the manner to bind POD to insoluble carriers, well-known physical and chemical methods are available, and no restriction is present with respect to the binding method.

Regarding luminol related compounds as chemiluminescent substrates, it is preferable to use luminol, isoluminol, N-ethylisoluminol, N-(4-aminobutyl)-N-ethylisoluminol-succinimide, N-(6-aminohexyl)-N-ethylisoluminol, 6-[N-(4-aminobutyl)-N-methylamino]-2,3-dihydro-1,4-phthalazinedione, and so on are considered. Among them, luminol and isoluminol are preferable to use, and in particular luminol is more preferable than isoluminol. Regarding the commercially available luminol, since reagent grade luminol is usually contaminated with hydrazine and sulfide, both of which are row materials for production, it is preferable to use luminol purified by repeated recrystallization.

In the present invention, it is preferable to carry out the chemiluminescent reaction in a weak basic solution, and especially pH of the solution is preferable within the range of 7 to 9. Any types of buffer solutions are available if those satisfy the pH conditions described above. Particularly, phosphate buffer solution, glycine/NaOH buffer solution, tris/HCl buffer solution, tris/acetate buffer solution, carbonate buffer solution, barbital buffer solution, borate buffer solution, and so on are considered as preferable buffer solutions.

The principle of the present invention is considered as follow. FIG. 5 shows the outline of the luminol-hydrogen peroxide-HRP (as a POD) reaction.

First, in the present system containing high concentration ammonium sulfate used in the present invention, it is considered that the protoheme on a POD molecule exists as a low-spin iron complex, carrying lone-paired electrons that readily make a coordinate bond with hydrogen peroxide.

Based on the spectroscopic data reported to date, it is known that the heme iron state in POD is usually in the high-spin state in the resting state. Although the heme iron exists as the high-spin complex irrespective of pH in the absence of ammonium sulfate, the spin state shifts to the low-spin state. That is, although the efficiency for hydrogen peroxide to make complex with the proto hem in the high-spin state is lower than that in the low-spin state, by shifting form the high-spin state to the low-spin one the reaction efficiency increases, i.e., the effect to accelerate the coordination of the heme iron to hydrogen peroxide in the active site of POD is expressed.

The change in the spin state of iron due to the presence of high concentration ammonium sulfate described just above is considered effective in the first reaction between HRP and $H_2O_2$ (hydrogen peroxide) in the reaction scheme shown in FIGS. 1A-1H.

Subsequently, the structure of water molecules is stabilized by the hydron bonding interaction between water molecules and both ammonium and sulfate ions dissociated from high concentration of ammonium sulfate, followed by the formation of the hydrophobic microenvironment even in the aqueous solution. As a result, it is considered that the reaction yield of the nucleophilic addition of $H_2O_2$ to luminol diazoquinone intermediate, followed by the efficient formation of luminol dioxetane product is enhanced.

The present invention also provides the solutions, consisting of luminol, POD and ammonium sulfate, for the detection and determination of POD and its activity measurement. Regarding the concentration of ammonium sulfate, it is preferable to be in the range of 3.0 M to 3.5 M. Both luminol and hydrogen peroxide are required to adjust the concentrations to become optimal for the determination of POD. For example, when POD is ranging in concentration between pM and nM, the concentration of hydrogen peroxide is preferably in the range between 10 mM to 100 mM, and on the other hand the luminol concentration is in the range of 2 mM to 10 mM. It is also necessary for pH to be within the range between 8 and 9.

Effects of Invention

Based on the present invention, higher sensitive detection and determination of POD becomes feasible even in the absence of the enhancer agent.

DESCRIPTION OF THE EMBODIMENTS

Figure 1B:
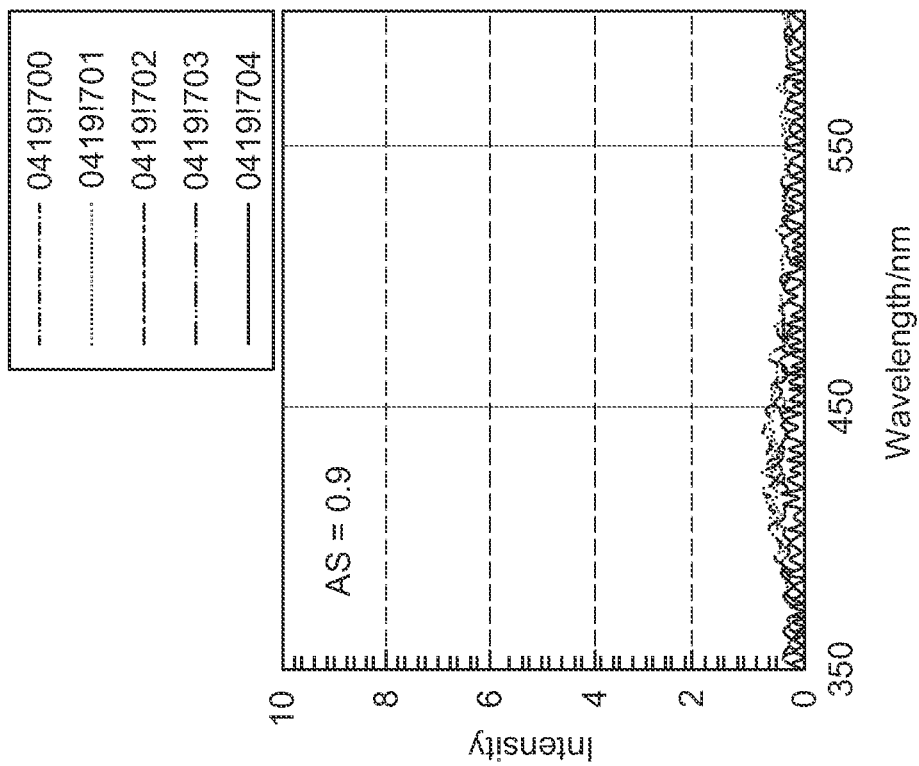
FIGS. 1A-AH Luminol chemiluminescence spectra recorded as a function of time in the presence of various concentrations of ammonium sulfate.
Figure 1A:
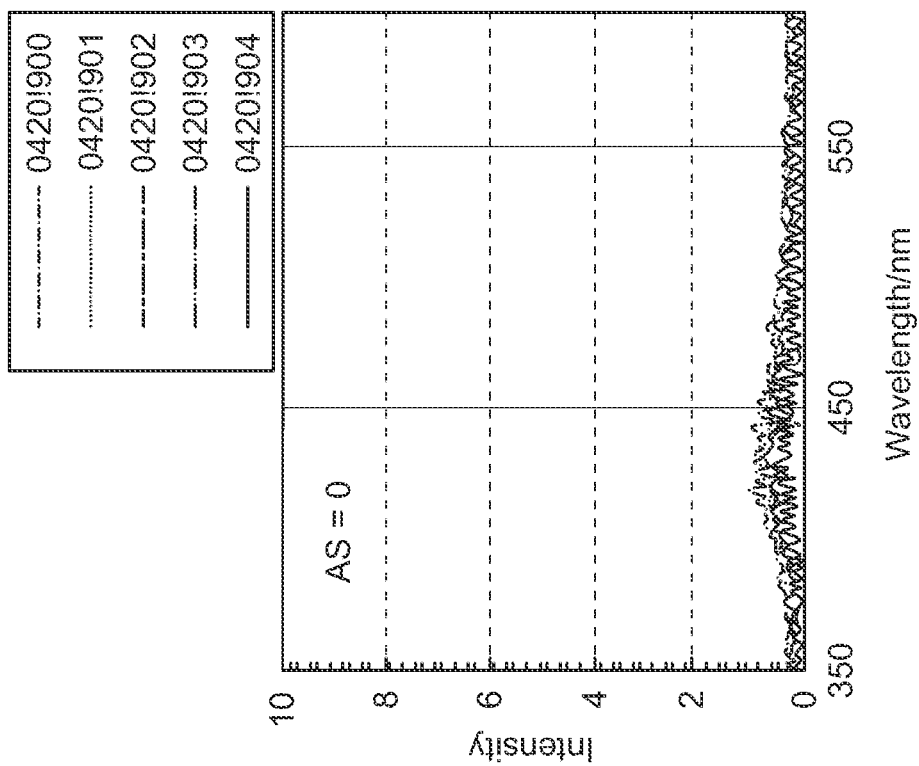
Figure 1D:
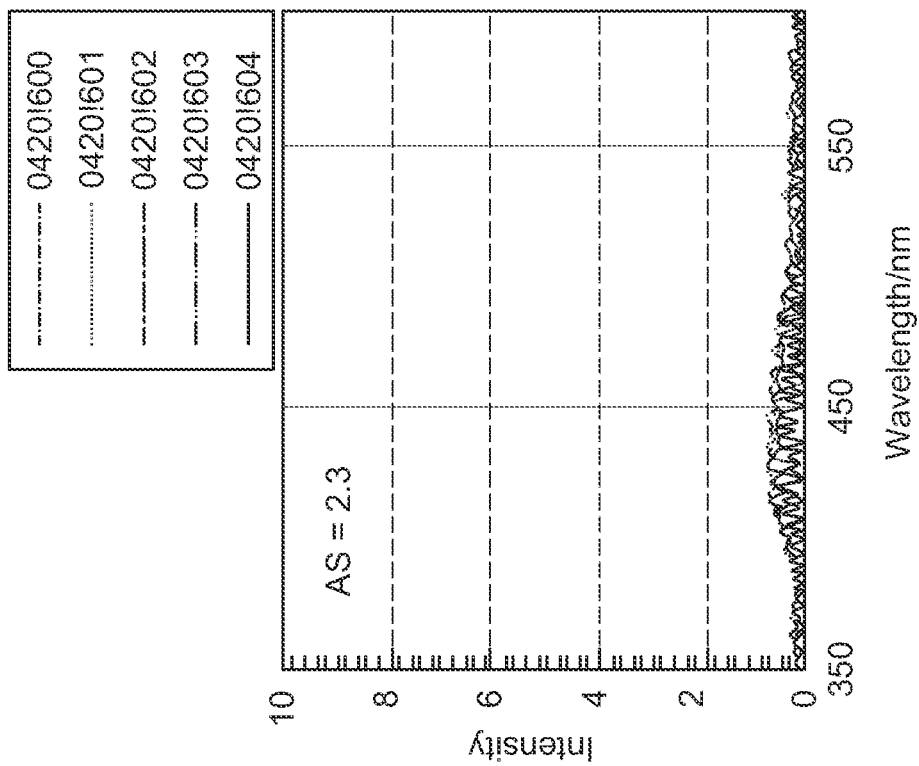
Figure 1C:
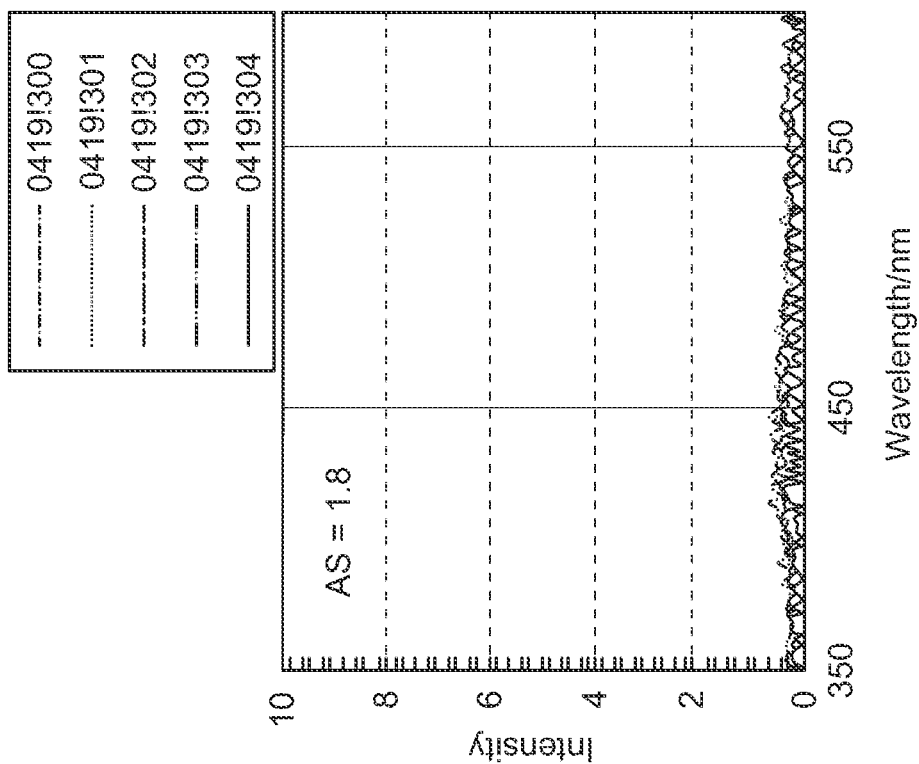
Figure 1F:
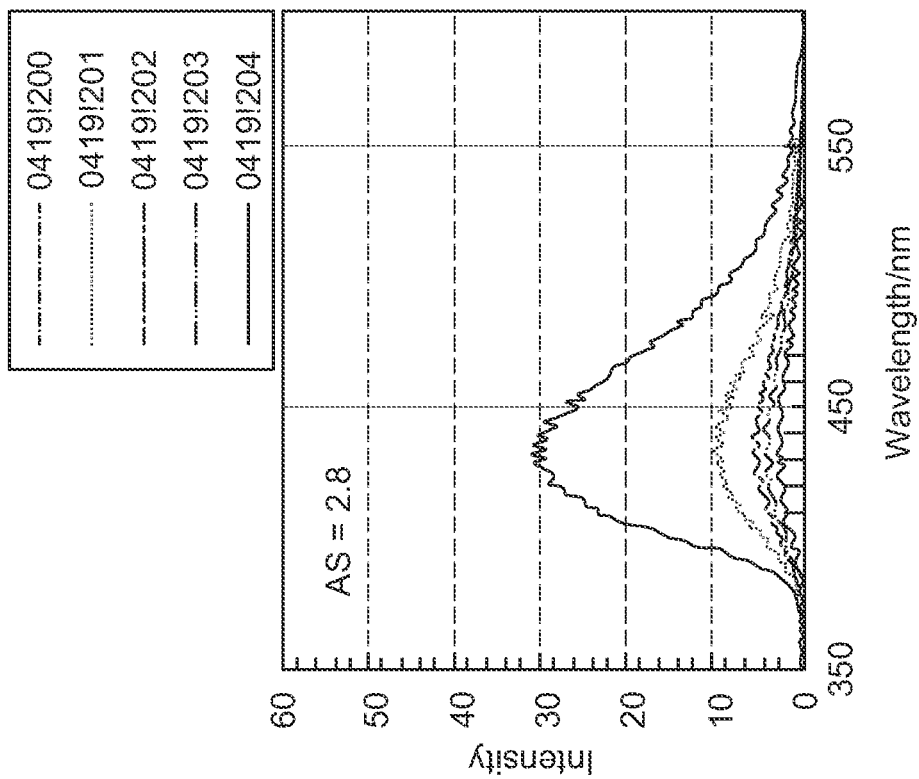
Figure 1E:
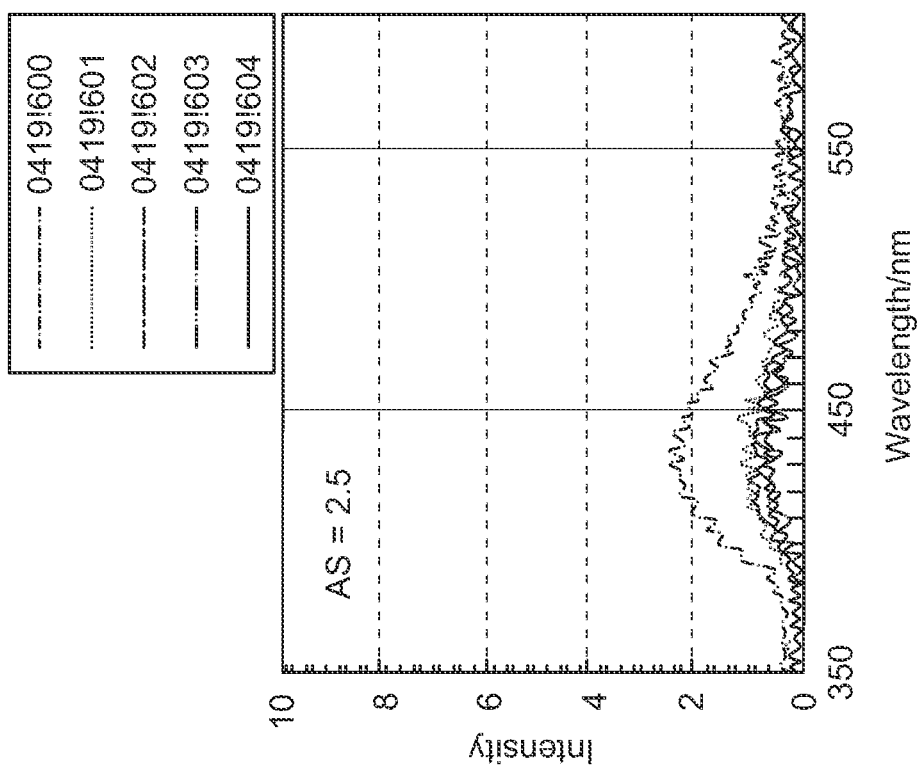
Figure 1H:
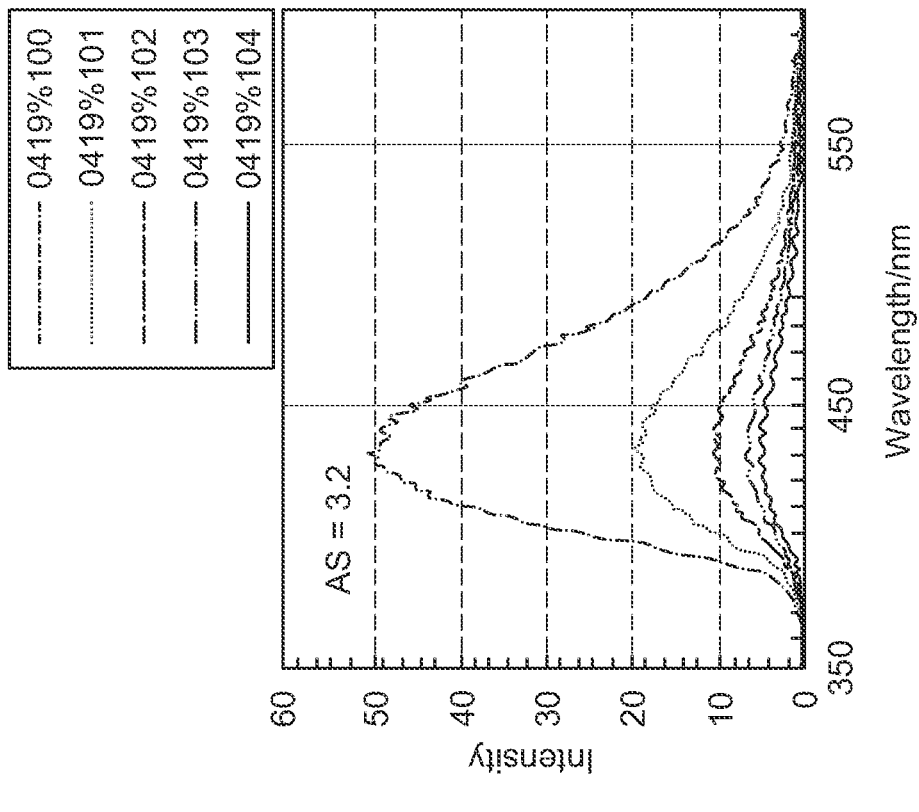
Figure 1G:
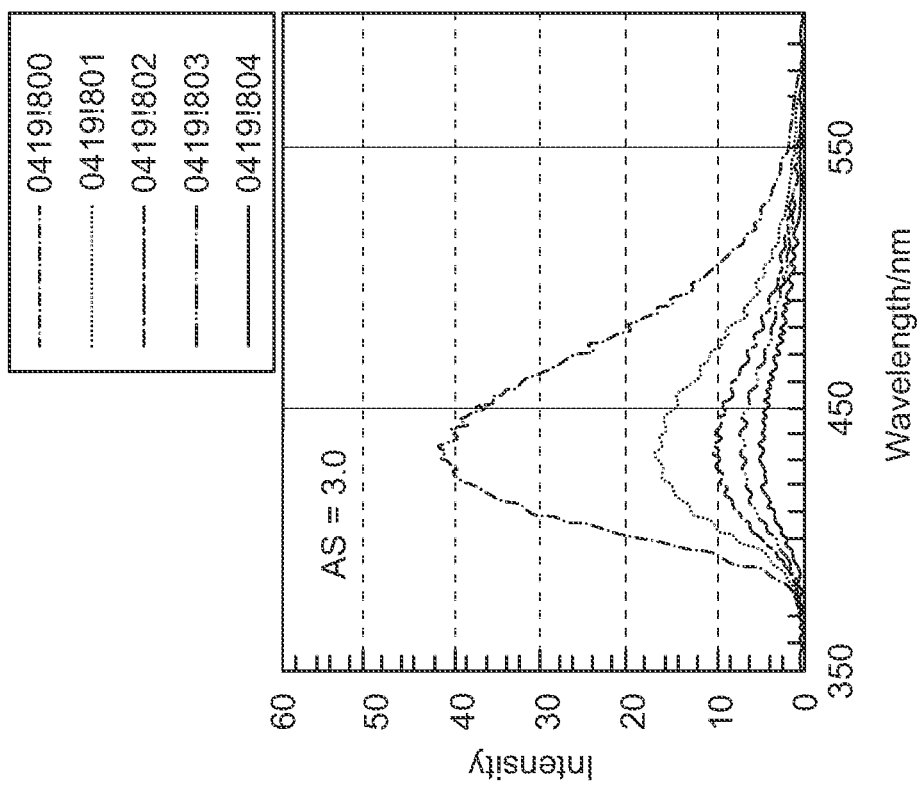

The present invention is explained in detail, as below.
General experimental conditions in the present invention are described as follows.

First, 1 μL of HRP standard solution ranging in concentration between $1\times10^{-6}$ M and $1\times10^{-9}$ M is placed in an empty 1-mL cuvette, subsequently 1000 μL mixture of equal parts of luminol solution and hydrogen peroxide solution is added to the cuvette to initiate the chemiluminescence reaction. Particularly, the concentrations of HRP, subjected to the evaluation of the present invention, is in the range of $5\times10^{-9}$ M to $1\times10^{-7}$ M. In this case, the concentration of HRP in the reaction mixture is in the range of $5\times10^{-12}$ M to $1\times10^{-10}$ M. Luminol solution used for the above-mentioned evaluation is the mixture of 1 vol of 30 mM luminol prepared in 0.75 M NaOH and 5 vol of pH8.5 tris(hydroxymethyl)aminomethane (0.1 M) buffer solution containing various concentrations of ammonium sulfate. The feature of this luminol solution is favorably prepared so as to make the final reaction mixture pH optimal. On the other hand, hydrogen peroxide solution used for the evaluation is various concentrations of ammonium sulfate solution containing 100 mM hydrogen peroxide: concentration of ammonium sulfate is corresponding to that used for luminol solution. The solution pH is in the range of 8.3 to 8.8. However, in the absence of ammonium sulfate, pH of the reaction mixture increases to approximately 12, because of the absence of buffer action by ammonium sulfate.

In the evaluation of the effect of ammonium sulfate (AS), luminol chemiluminescence was characterized at various molar concentrations of AS using the reaction system described above. Specifically, the effect was evaluated by using the light intensity calculated from the chemiluminescence spectra recorded as a function of time. Chemiluminescence spectra was repeatedly recorded 5 times at one minute interval. First spectral measurement was carried out at 10 s after the initiation of the chemiluminescence reaction, i.e., five spectra were obtained at 0.17 min (corresponding to a00 designated in FIGS. 1, 2 and 4), 1.17 min (a01), 2.17 min (a02), 3.17 min (a03), and 4.17 min (a04); the third digit is expressed as "a". For example, in FIGS. 1A-1H, correspondence between legend for each spectrum and time is as follows; 0420! 900→0.17 min, 901→1.17 min, 902→2.17 min, 903→3.17 min, 904→4.17 min.

FIGS. 1A-1H show chemiluminescence spectra recorded at various concentrations of ammonium sulfate used to prepare pH8.5 tris (0.1 M) buffer solution and hydrogen peroxide solutions: (a) AS=0.0 M, (b) AS=0.9 M, (c), AS=1.8 M, (d) AS=2.3 M, (e) AS=2.5 M, (f) AS=2.8 M, (g) AS=3.0 M, and (h) AS=3.2 M. As shown in FIGS. 1A-1H, the intensity of the chemiluminescence spectra is intensified with an increase in the ammonium sulfate concentration. The intensity obtained at 3.2 M ammonium sulfate is intensified by 100 times as compared to that obtained in the ammonium sulfate free system. In FIGS. 1A-1H, it is shown that the weak chemiluminescence is observed in the absence of ammonium sulfate. This is possibly because iron (III) ion liberated from HRP in the relatively high pH solution catalyzes the luminol chemiluminescence but not from the HRP catalyzed luminol reaction. It is possible to achieve 200 times intensification of chemiluminescence by adjusting the concentrations of luminol and hydrogen peroxide in the solution. FIGS. 1A-1H shows changes in chemiluminescence spectra recorded at 1-min interval in the presence of various concentrations of ammonium sulfate (AS). First spectral measurement was carried out at 10 s after the initiation of the chemiluminescence reaction, i.e., five spectra were obtained at 0.17 min (corresponding to a00 designated on the graphs in FIGS. 1A-1H, 2 and 4), 1.17 min (a01), 2.17 min (a02), 3.17 min (a03), and 4.17 min (a04); the third digit is expressed as "a". For example, in FIGS. 1A-1H, correspondence between legend for each spectrum and time is as follows; 0420!900→0.17 min, 901→1.17 min, 902→2.17 min, 903→3.17 min, 904→4.17 min.

The Integrated intensity (area under each spectrum) vs. Time elapsed after the initiation of the reaction.

317 #800; [HRP]=0
800 (10 s after), #801 (1.17 min after), #802 (2.17 min after), #803 (3.17 min after), #804 (4.17 min after),
317 #600; [HRP]=$5\times10^{-12}$ M
600 (10 s after), #601 (1.17 min after), #602 (2.17 min after), #603 (3.17 min after), #604 (4.17 min after),
317 #100; [HRP]=$1\times10^{-10}$ M
100 (10 s after), #101 (1.17 min after), #102 (2.17 min after), #103 (3.17 min after), #104 (4.17 min after)

Figure 2:
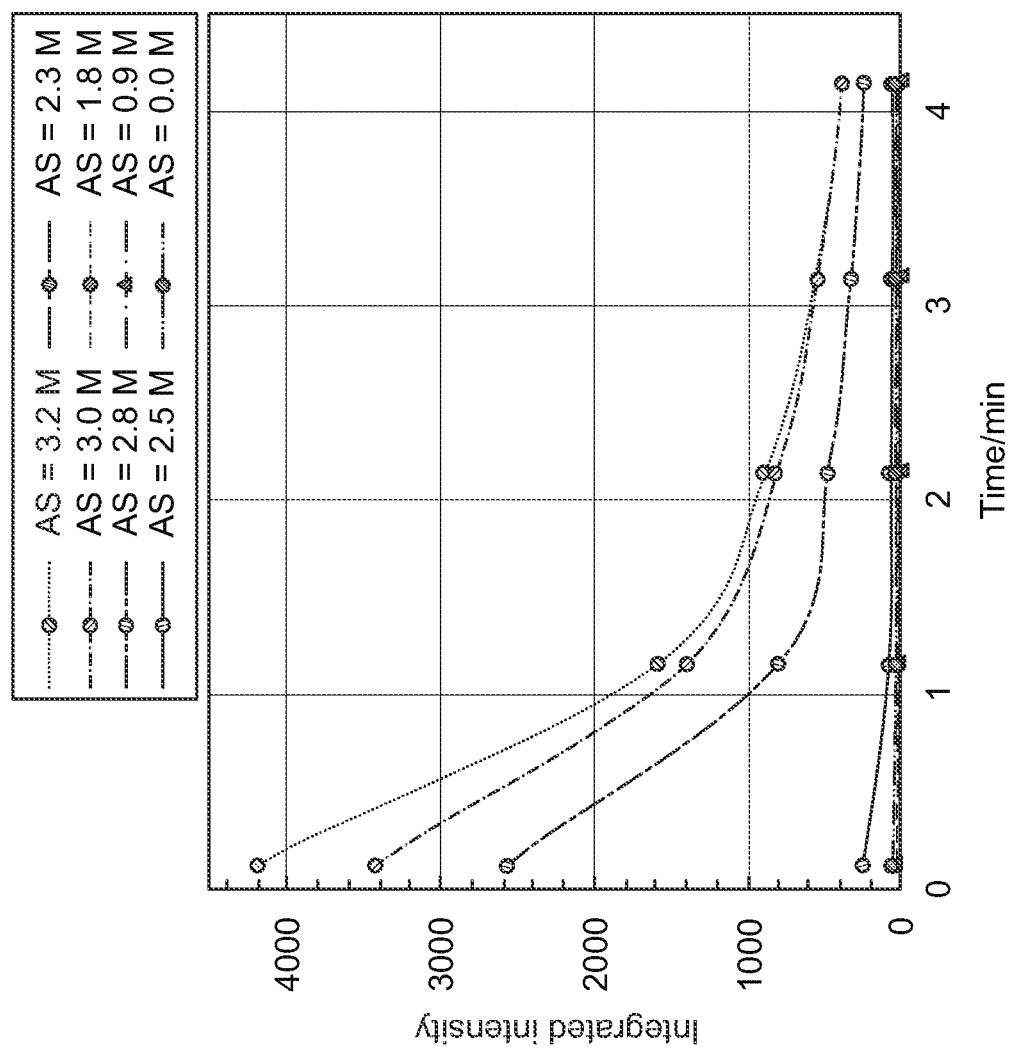
FIG. 2 Plots of the integrated intensity (area under each spectrum) of luminol chemiluminescence recorded in the presence of various concentrations of ammonium sulfate against time elapsed after the initiation of the reaction.
Figures 3A, 3B:
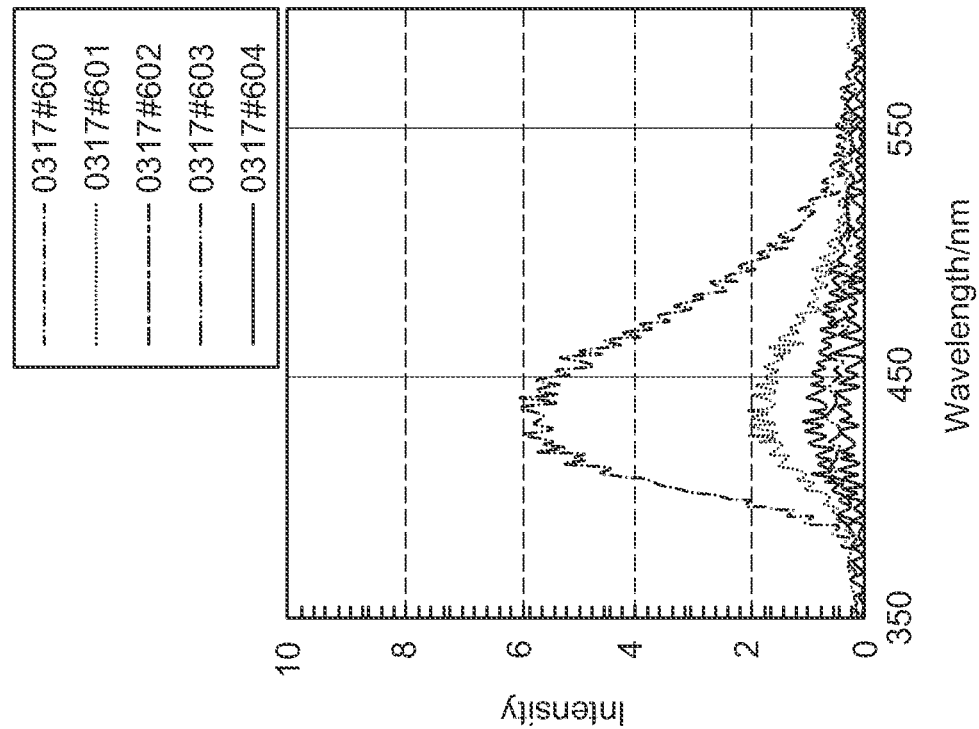
FIGS. 3A-3D Detection and determination of HRP based on the present chemiluminescence under the optimal conditions.
Figure 3D:
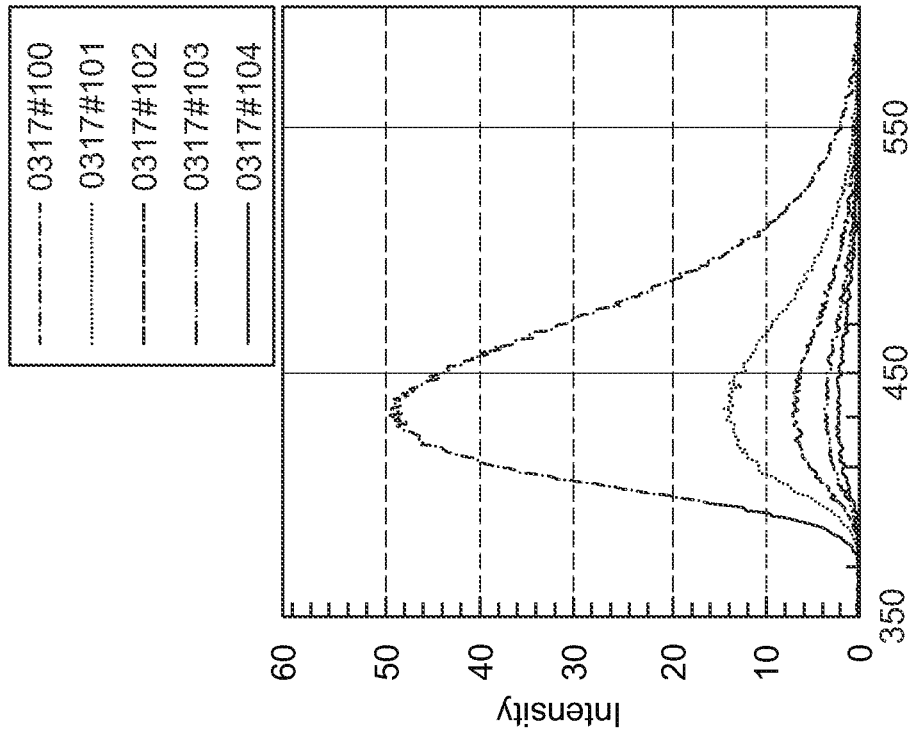
Figure 3C:
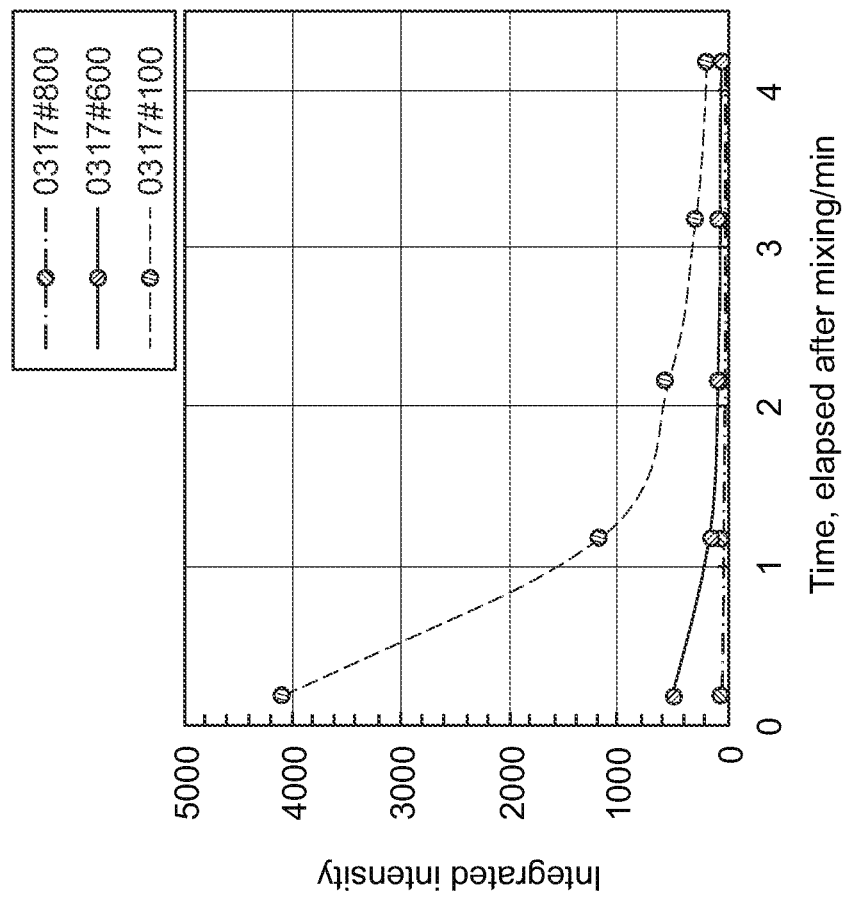

FIG. 2 exhibits the relationship between the luminol chemiluminescence intensity recorded at various concentrations of ammonium sulfate and time elapsed after the initiation of the reaction. In FIG. 2, each integrated intensity (=area under each spectrum) is plotted as a function of time elapsed. It is shown that the intensity is evidently increased, especially when the AS concentration is greater than 3.0 M. FIG. 2 shows plots of the integrated intensity (area under each spectrum) of the luminol chemiluminescence generated in the presence of various concentrations of ammonium sulfate (AS) against time elapsed after the initiation of the reaction.

It is clearly shown in FIG. 2 that the effect of AS on the chemiluminescence becomes remarkable when the AS concentration is greater than approximately 2.8 M. This means that the threshold value is present to express the effect of AS. This result also suggests that AS markedly affects the reaction mechanism. That is, it can be concluded that high concentration AS contributes to accelerate two reactions in the reaction mechanism, resulting in the increase in the overall reaction rate, followed by the increase in the chemiluminescence intensity.

FIGS. 3A-3D exhibit that the results obtained under the optimal conditions (concentration in the reaction mixture; AS=3.2 M, luminol=2.5 M, and $H_2O_2$=50 mM). Based on the present method, detection, and determination of pM level of HRP become feasible.

FIGS. 3A-3D show a detection and determination of HRP. It is possible to detect and determine pM level of HRP at high SN ratio. The chemiluminescence spectra, are repeatedly recorded 5 times at 1-min interval. First spectral measurement was carried out at 10 s after the initiation of the chemiluminescence reaction.

317 #100, 317 #600, 317 #800—about 10 s (0.17 min) after the initiations of the reaction 317 #101, 317 #601, 317 #801—1.17 min 317 #102, 317 #602, 317 #802—2.17 min 317 #103, 317 #603, 317 #803—3.17 min The Integrated intensity (area under each spectrum vs. Time elapsed after the initiation of the reaction is shown.

317 #800; [HRP]=0

800 (10 s after), #801 (1.17 min after), #802 (2.17 min after), #803 (3.17 min after), #804 (4.17 min after),

317 #600; [HRP]=5×10-12 M

600 (10 s after), #601 (1.17 min after), #602 (2.17 min after), #603 (3.17 min after), #604 (4.17 min after),

317 #100; [HRP]=1×10-10 M

100 (10 s after), #101 (1.17 min after), #102 (2.17 min after), #103 (3.17 min after), #104 (4.17 min after)

Figure 4:
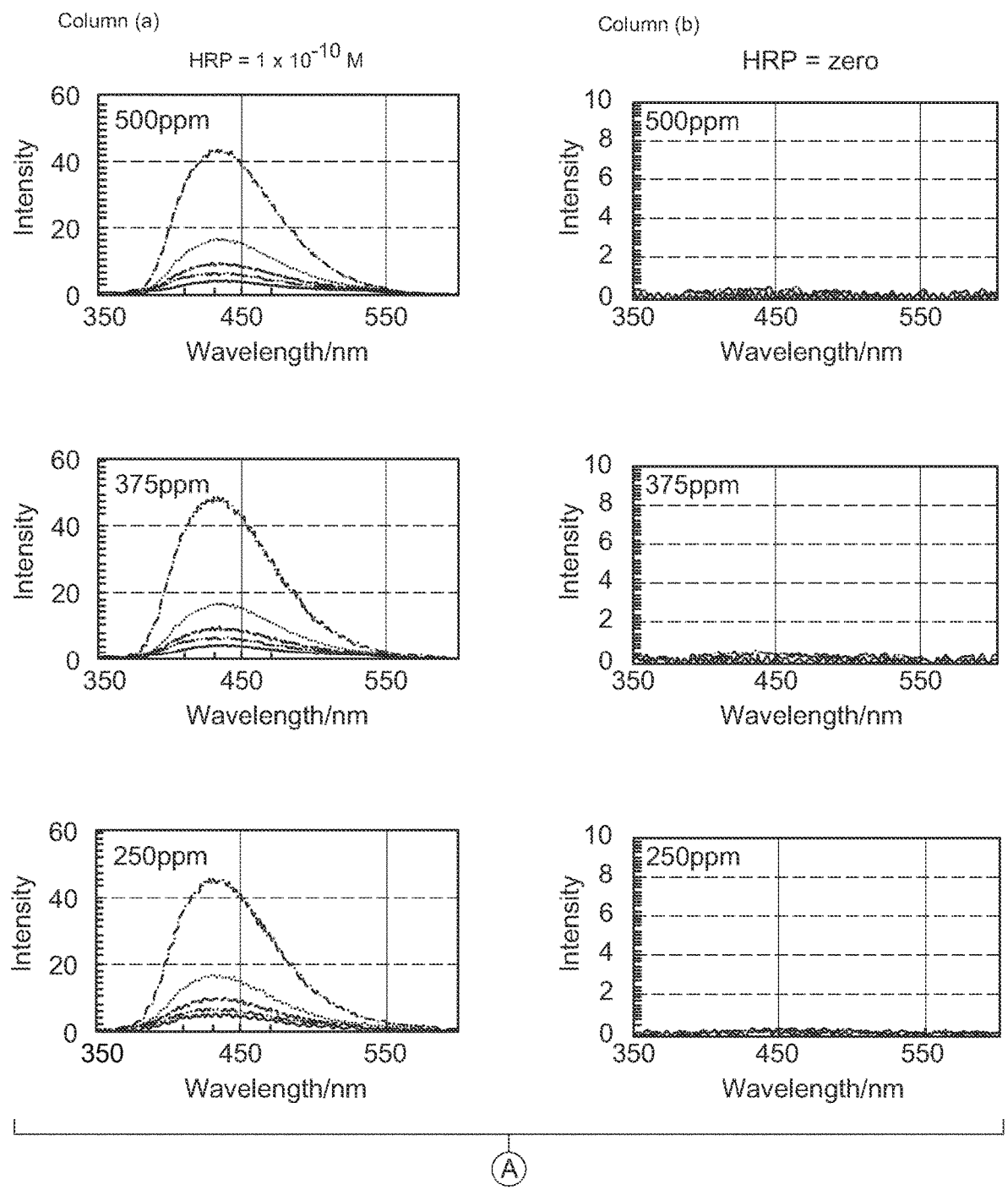
FIG. 4 Effect of EDTA on the removal of background chemiluminescence. EDTA concentration (ppm) is indicated on each graph.

Subsequently, the effect of ethylenediamine-tetraacetic acid (EDTA) added to the present reaction solution on the chemiluminescence was examined. The results obtained are shown in FIG. 4. The concentrations of ammonium sulfate, luminol, and hydrogen peroxide are 3.2 M, 2.5 mM, and 50 mM, respectively. These concentrations are common to all experiments in this examination. FIG. 4 shown the effect of EDTA on the removal of background chemiluminescence. EDTA concentration (ppm) in the reaction mixture is indicated on each panel.

The concentration of each component is indicated in FIG. 4. Graphs shown in the left column (column (a)) are obtained in the presence of $1 \times 10^{-10}$ M HRP, and on the other hand, graphs in the right column (column (b)) are obtained in the absence of HRP. It is clearly shown that background chemiluminescence is almost completely removed in the systems to which EDTA is added. Therefore, it can be regarded that the chemiluminescence observed in the presence of EDTA (FIG. 4, column (a)) is arising from the HRP catalyzed luminol reaction. The bottom graph in column (b) is obtained in the absence of not only EDTA but also HRP. Despite being that HRP is not present, chemiluminescence is observed. This is possibly due to background chemiluminescence attributed to the trace amount of metal ions contained in ammonium sulfate as impurity. This background can be fully removed by masking effect for contaminant metal ions with EDTA, originally added to stabilize hydrogen peroxide for the long-term storage. Furthermore, it is evident that EDTA does not exert any harmful effect on the luminol—$H_2O_2$—HRP chemiluminescence intensified in the presence of ammonium sulfate.

Figure 5:
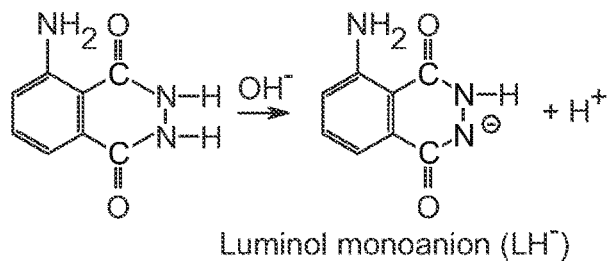
FIG. 5 Reaction mechanism for the Luminol—$H_2O_2$—HRP reaction.
Figure 5:
Figure 5:
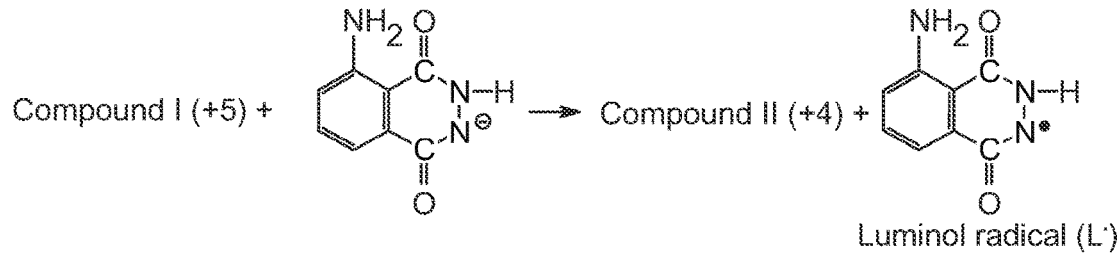
Figure 5:
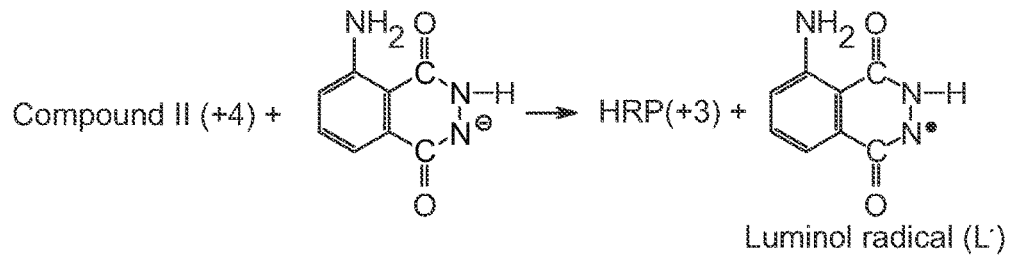

FIG. 5 shows a reaction mechanism for the luminol—H2O2—peroxidase chemiluminescence reaction.

INDUSTRIAL APPLICABILITY

According to the present study, the present chemiluminescence system is available to detect and determine against all types of analytes. For example, the present method is available for the chemiluminescent detection, determination, and activity measurement of peroxidase, which is useful in the detection of biological macromolecules, organic substances and so on.

What is claimed:

1. A method for detection, determination, and activity measurement of peroxidase using luminol as its substrate comprising:
    dissolving ammonium sulfate in a reaction solution comprising peroxidase and luminol at a concentration of 3 M to 3.5 M.

2. The method for detection, determination, and activity measurement of peroxidase using luminol according to claim 1, wherein ethylenediaminetetraacetate is dissolved together with ammonium sulfate.

3. A solution for detection, determination, and activity measurement of peroxidase comprising:
    luminol, hydrogen peroxide, peroxidase, and ammonium sulfate; wherein ammonium sulfate has a concentration of 3 M to 3.5 M.

* * * * *